US 6,296,651 B1

(12) United States Patent
Lary et al.

(10) Patent No.: US 6,296,651 B1
(45) Date of Patent: *Oct. 2, 2001

(54) METHOD OF USING NEOVASCULARIZATION CATHETER

(75) Inventors: Banning Gray Lary, Miami, FL (US); Herbert R. Radisch, Jr., San Diego, CA (US)

(73) Assignee: Interventional Technologies, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/520,070

(22) Filed: Mar. 7, 2000

Related U.S. Application Data (60) Division of application No. 09/123,758, filed on Jul. 27, 1998, now Pat. No. 6,117,153, which is a continuation-in-part of application No. 08/726,401, filed on Oct. 3, 1996, now Pat. No. 5,800,450.

(51) Int. Cl.[7] ................................. A61B 17/32
(52) U.S. Cl. ................................. 606/170; 606/167
(58) Field of Search ................ 606/170–171, 606/159, 1, 7, 167, 185, 108, 198; 608/96–104; 604/264; 128/898

(56) References Cited

U.S. PATENT DOCUMENTS

| | | |
|---|---|---|
| 3,512,519 | 5/1970 | Hall . |
| 3,605,721 | 9/1971 | Hallac . |
| 3,990,453 | 11/1976 | Douvas et al. . |
| 4,195,637 | 4/1980 | Gruntzig et al. . |
| 4,441,509 | 4/1984 | Kotsifas et al. . |
| 4,582,181 | 4/1986 | Samson . |
| 4,589,412 | 5/1986 | Kensey . |
| 4,690,140 | 9/1987 | Mecca . |
| 4,696,667 | 9/1987 | Masch . |
| 4,708,147 | 11/1987 | Haaga . |
| 4,728,319 | 3/1988 | Masch . |
| 4,757,826 | 7/1988 | Abdulhay . |
| 4,765,332 | 8/1988 | Fischell et al. . |
| 4,887,613 | 12/1989 | Farr et al. . |
| 4,926,858 | 5/1990 | Gifford, III et al. . |
| 4,966,604 | 10/1990 | Reiss . |
| 5,135,484 | 8/1992 | Wright . |
| 5,287,861 | 2/1994 | Wilk . |
| 5,312,341 | 5/1994 | Turi . |
| 5,325,860 | 7/1994 | Seward et al. . |
| 5,372,588 | 12/1994 | Farley et al. . |
| 5,454,782 | 10/1995 | Perkins . |
| 5,507,795 | 4/1996 | Chiang et al. . |
| 5,669,920 | 9/1997 | Conley et al. . |
| 5,674,232 * | 10/1997 | Halliburton ............... 606/159 |
| 5,697,944 | 12/1997 | Lary . |
| 5,800,450 | 9/1998 | Lary et al. . |
| 5,891,133 * | 4/1999 | Murphy-Chutorian ......... 606/7 |
| 6,102,046 * | 8/2000 | Weinstein et al. ........... 128/898 |

FOREIGN PATENT DOCUMENTS

| | | |
|---|---|---|
| 0 551 707 A1 | 7/1993 | (EP) . |
| 0 647 434 A2 | 4/1995 | (EP) . |
| 0 721 766 A1 | 7/1996 | (EP) . |
| PCT/US91/ 08388 | 6/1992 | (WO) . |

* cited by examiner

Primary Examiner—Kennedy Schaetzle
Assistant Examiner—Kristen Droesch
(74) Attorney, Agent, or Firm—Nydegger & Associates (57) ABSTRACT

The present invention is a device and a method for boring a perfusion channel from a coronary artery into a cardiac muscle of a patient. Structurally, the present invention includes a positioning catheter, anchor means and a cutting catheter. The cutting catheter includes a plurality of blades and is advanceable through a deployment lumen of the positioning catheter. Advancement of the cutting catheter through the deployment lumen causes a distal end of the cutting catheter to project laterally from the positioning catheter. In use, the positioning catheter is positioned within the coronary artery. The anchor means is then expanded to anchor the positioning catheter within the artery. The cutting catheter is then advanced through the deployment lumen to bore one or more perfusion channels in the myocardial tissue.

9 Claims, 7 Drawing Sheets

METHOD OF USING NEOVASCULARIZATION CATHETER

This Application is a Divisional of application Ser. No. 09/123,758, filed Jul. 27, 1998, now U.S. Pat. No. 6,117,153, and which is a Continuation-in-Part of application Ser. No. 08/726,401, filed Oct. 3, 1996, which issued as Pat. No. 5,800,450, on Sep. 1, 1998. The contents of U.S. Pat. Nos. 6,117,153 and 5,800,758 are incorporate herein by reference.

FIELD OF THE INVENTION

The present invention pertains generally to surgical devices and procedures. More particularly, the present invention pertains to a device and method for treating occlusions in the coronary artery which inhibit blood flow to the heart.

BACKGROUND

Many medical complications are created by the total or even partial blockage of blood vessels of the body. For example, it is relatively common for stenotic segments to develop in the arterial vessels which supply blood to the heart. These stenotic segments may partially or fully occlude the vessels, thereby decreasing cardiac capacity and/or causing myocardial infarction.

Numerous methods and devices have been developed to treat or remove stenotic segments which occur within the internal vessels of the body. For example, an angioplasty procedure is commonly used to treat the blockages in vessels. Typically, angioplasty generally involves inflation of a tubular balloon within the stenotic segments which occlude a particular vessel. Inflation of the balloon dilates the stenotic segment and fully or partially restores the flow of blood within the involved vessel.

Atherectomy is another procedure which has been developed to clear stenotic segments from occluded vessels. In an atherectomy procedure, a rotatable cutting tool is advanced through the stenotic segments which occlude a particular vessel. The rotating cutter severs the material forming the stenotic segment, and allows the severed stenotic material to be removed by operation of a vacuum or other means.

Unfortunately, stenotic segments can develop in areas where angioplasty and atherectomy techniques can not be utilized. For example, the development of a stenotic segments within a vessel which is internal to an organ, presents special problems which may not be suited for treatment by traditional angioplasty and atherectomy procedures. Specifically, stenotic segments can develop within the internal vessels of the heart. Because these vessels provide blood and oxygen to the myocardial tissue, occlusions which develop within these internal vessels present a serious risk to the health of the patient. As indicated above, the size and location of many of these vessels makes treatment with traditional methods and devices, such as angioplasty and atherectomy, difficult and generally ineffective.

In light of the above, it is an object of the present invention to provide a device and method for treating occlusions in the internal vessels of an organ. Another object of the present invention is to provide a device and method for treating an occlusion in a coronary artery which inhibits blood flow to the myocardial tissue of the heart. Still another object of the present invention is to provide a device for treating occlusions in the coronary artery which is relatively simple to manufacture, easy to use, and comparatively cost effective.

SUMMARY

The present invention is directed to a device and method adapted for creating one or more new pathways from a vessel into an organ for the flow of blood. More specifically, the present invention is a device for creating one or more channels from the coronary artery into the cardiac muscle of the heart to enhance the flow of blood from the coronary artery into the cardiac muscle. This enhances cardiac capacity and inhibits myocardial infarction.

Structurally, the present invention includes a positioning catheter, anchoring means and a cutting catheter. The positioning catheter is formed with a deployment lumen. The deployment lumen includes a plurality of deployment apertures which extend through the catheter into the deployment lumen.

The anchor means secures the positioning catheter within the vessel around a circumference of the vessel, so that the cutting catheter can precisely create the perfusion channel. In one version, the anchor means is a cylindrical sleeve attached to the positioning catheter. The sleeve has a distal sleeve end and a proximal sleeve end which are adapted to move relative to each other. Functionally, the movement of the distal sleeve end towards the proximal sleeve end causes the sleeve to expand radially outward. Alternately, in a second version of the present invention, the anchor means is an inflatable balloon attached to the positioning catheter.

The cutting catheter is designed to incise and dilate the tissue of the cardiac muscle. Preferably, the cutting catheter includes a cutting catheter body having a plurality of spaced apart cutting blades. The blades extend radially around the cutting catheter body and are aligned with the longitudinal axis of the cutting catheter body. The blades may be fixedly attached to the surface of the cutting catheter body or each blade may be retractable into the cutting catheter body. In cases where the blades are retractable, each blade is preferably spring-loaded, or otherwise biased, to move from a first position where the blades are substantially contained within the cutting catheter to a second position where the blades extend from the surface of the cutting catheter body. This feature causes the blades to extend from the cutting catheter when the cutting catheter body extends from the positioning catheter.

The cutting catheter may be formed to include a cutting catheter lumen for receiving a cutting guidewire. Generally, the cutting guidewire is formed from a resilient and flexible metal, such as stainless steel, and has a sharpened distal end. The cutting guidewire is insertable through the cutting catheter lumen to allow the sharpened distal end of the cutting guidewire to be selectively extended from the cutting catheter. The cutting guidewire can also be formed with a cutting guidewire lumen so that a medication can be released into the muscle. Alternately, a contrast medium can be released from the cutting guidewire lumen and/or a pressure measurement can be taken with the cutting guidewire lumen to ensure that the cutting catheter is properly positioned in the cardiac muscle.

Operationally, the positioning catheter is first advanced into the coronary artery which supplies blood to the cardiac muscle. The advancement of the positioning catheter continues until a distal end of the positioning catheter is located within boundaries of the heart itself and the deployment aperture of the positioning catheter is located adjacent to the site where a new perfusion channel is to be formed. With the positioning catheter positioned at the proper location, the anchoring means is expanded to contact the artery to anchor the positioning catheter within the artery.

Subsequently, the cutting guidewire is inserted through the deployment lumen and one of the deployment apertures into the myocardial tissue. A contrast medium can be released or a pressure measurement can be taken to ensure that the cutting guidewire is properly positioned. Next, the cutting catheter is inserted into the deployment lumen over the cutting guidewire. This causes the blades to adopt the first position where each blade is positioned within the cutting catheter body. The cutting catheter is then advanced through the deployment lumen. As a distal end of the cutting catheter emerges from one of the deployment apertures, the spring-loaded blades adopt the second position where each blade extends from the surface of the cutting catheter body. Further, advancement of the cutting catheter and the cutting guidewire forces the cutting catheter to bore a channel through the myocardial tissue. The boring of the channel is aided by the blades which incise the myocardial tissue to accommodate the advancing cutting catheter.

At any time during advancement of the cutting catheter, the cutting guidewire may be advanced through the cutting catheter lumen in the myocardial tissue, thereby boring a path, or pilot hole, for subsequent advancement of the cutting catheter. The process of alternately advancing the cutting guidewire and cutting catheter may be repeated until one or more channels through the myocardial tissue have reached the desired depth.

Once the cutting catheter has been fully advanced, the cutting catheter may be removed from the patient and extended from an alternate deployment aperture into the myocardial tissue to create another perfusion channel. In some cases it will be preferable to position a vascular stent at the junction between the involved artery and the newly created perfusion channel. In such cases a self-expanding stent may be advanced through the deployment lumen to be emitted at the orifice formed near the positioning catheter's distal end. As the stent leaves the orifice, it may be expanded to support the newly formed perfusion channel.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION

Figure 1:
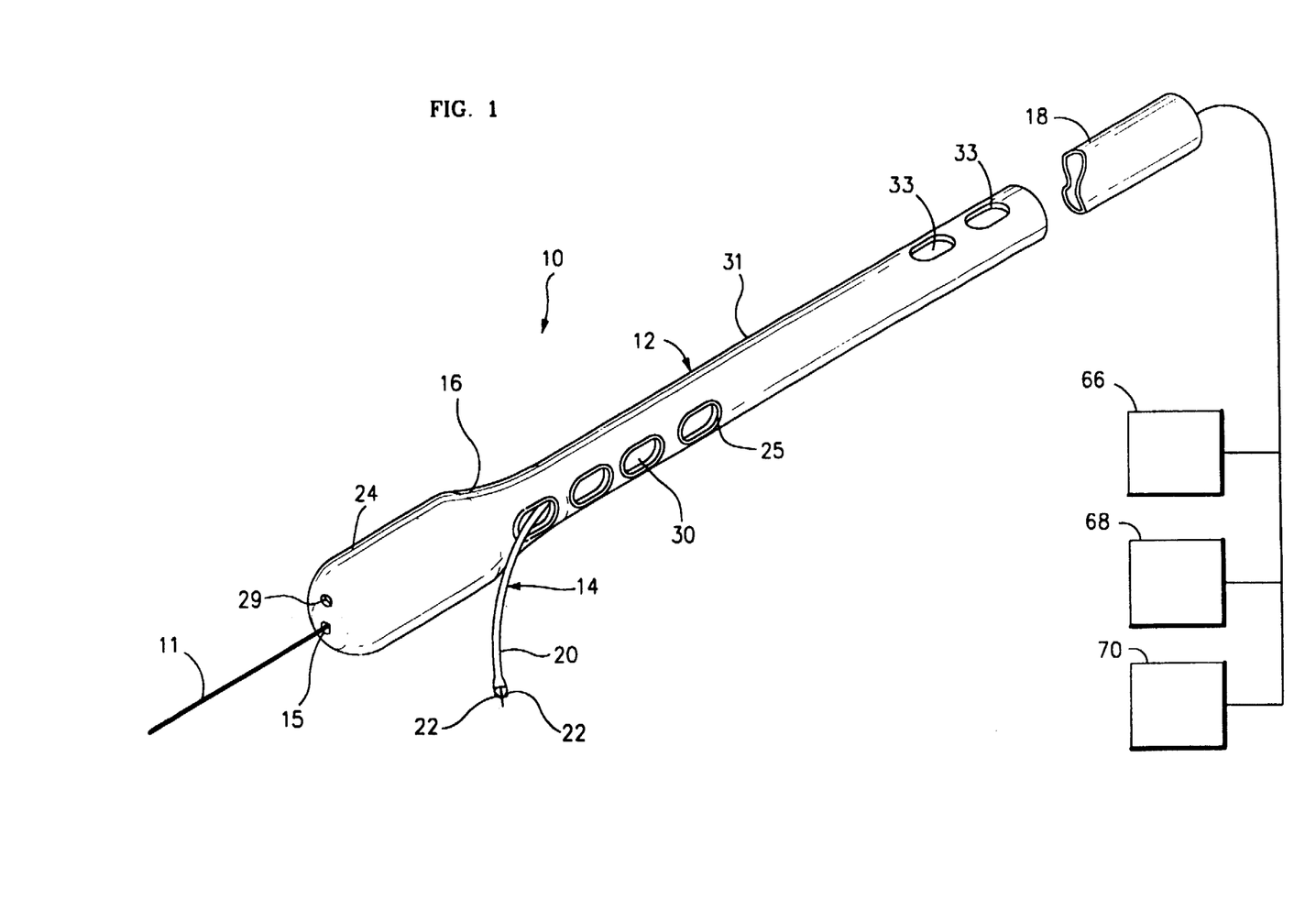
FIG. 1 is an isometric view of a device having features of the present invention.

Referring initially to FIG. 1, a device 10 having features of the present invention includes a positioning guidewire 11, a positioning catheter 12 and a cutting catheter 14. Structurally, the positioning guidewire 11 extends through a positioning guidewire lumen 15 in the positioning catheter 12. The positioning catheter 12 is formed to have a cylindrical or otherwise elongated shape and has a distal end 16 and a proximal end 18. Preferably, the positioning catheter 12 is formed from a flexible and somewhat stiff material. The cutting catheter 14 is also formed to have a cylindrical or otherwise elongated shape and has a distal end 20. Preferably, the cutting catheter 14 is formed from a flexible and somewhat resilient material. A series of blades 22 are mounted substantially radially around the distal end 20 of the cutting catheter 14. FIG. 1 also shows an anchor means 24 that is mounted to the distal end 16 of the positioning catheter 12.

Figure 2:
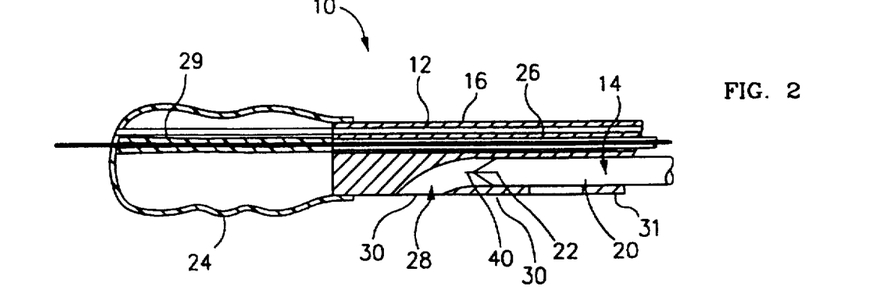
FIG. 2 is a cross-sectional view of the distal portion of the positioning catheter with a cutting catheter withdrawn and held within a deployment lumen.
Figure 3:
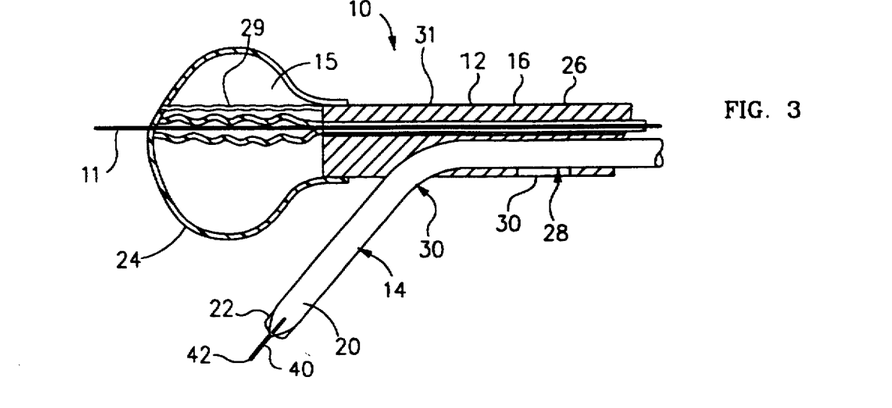
FIG. 3 is a cross-sectional view of the positioning catheter illustrating an inflatable balloon shown in an expanded configuration and the cutting catheter advanced to project from the positioning catheter.

The structural details of one embodiment of the present invention may be better appreciated with reference to FIGS. 2 and 3, where it may be seen that the positioning catheter 12 is formed to surround an inflation lumen 26, a deployment lumen 28, and a bypass lumen 29. The inflation lumen 26 passes between the distal end 16 and the proximal end 18 (shown in FIG. 1) of the positioning catheter 12. At the distal end 16 of the positioning catheter 12, the inflation lumen 26 is connected in fluid communication to the anchor means 24, i.e., an inflatable balloon. As a result, fluid may be passed through the inflation lumen 26 from a pressurized fluid source (not shown) to selectively inflate the anchor means 24. Inflation of this nature may be appreciated by comparison of FIG. 2, where the balloon is shown in an uninflated state and of FIG. 3, where the balloon has been partially inflated.

The deployment lumen 28 extends between the proximal end 18 of the positioning catheter 12 toward the distal end 16 of the positioning catheter 12. A plurality of spaced apart deployment apertures 30 are positioned near the distal end 16 of the positioning catheter 12. Each of the deployment apertures 30 are oriented radially outward and distally from the positioning catheter 12. Each deployment aperture 30 extends from a catheter outer surface 31 of the positioning catheter 12 into the deployment lumen 28. The embodiment illustrated in FIG. 1 includes four (4) longitudinally, spaced apart deployment apertures 30. However, those skilled in the art should recognize that the number and space between adjacent deployment apertures 30 can be varied.

The cutting catheter 14 is advanced through the deployment lumen 28 until the distal end 20 of the cutting catheter 14 extends from one of the deployment apertures 30. Advancement of this nature may be appreciated by comparison of FIGS. 2 and 3. In more detail, it may be seen in FIG. 2, that the cutting catheter 14 is fully contained within the deployment lumen 28. In FIG. 3, however, the cutting catheter 14 has been advanced to project the distal end 20 of the cutting catheter 14 from one of the deployment apertures 30.

The shape and orientation of the deployment apertures 30 direct the cutting catheter 14 in a general direction which is radially outward and distally forward from the positioning catheter 12. It may be appreciated that the cutting catheter 14 may be advanced more or less than the advancement shown in FIG. 3. Further, it should be appreciated that once the anchor means 24 secures the positioning catheter 12, the cutting catheter 14 may be advanced from any one of the deployment apertures 30. Moreover, the distal end 20 of the cutting catheter 14 may be projected a variable and selectable distance from the positioning catheter 12. The projection of the cutting catheter 14 from the positioning catheter 12 is subsequently followed by the withdrawal of the cutting catheter 14 into the deployment lumen 28 of the positioning catheter 12. Preferably, a radiopaque deployment marker 25 (illustrated in FIG. 1) is positioned by each deployment aperture 30, so that the position of each deployment aperture 30 in the patient can be quickly evaluated. In the embodiment illustrated in FIG. 1, the deployment marker 25 encircles each deployment aperture 30.

Referring to FIGS. 2 and 3, the bypass lumen 29 allows for the flow of blood pass the anchor means. Thus, blood flow to and from the heart is not completely interrupted during this procedure. As illustrated in FIGS. 2 and 3, the bypass lumen 29 extends through the anchor means 24 and into the positioning catheter 12. With reference to FIG. 1, a pair of outlet apertures 33 extend through the catheter outer surface 31 into the bypass lumen to allow for the flow of blood pass the anchor means 24.

Figure 4:
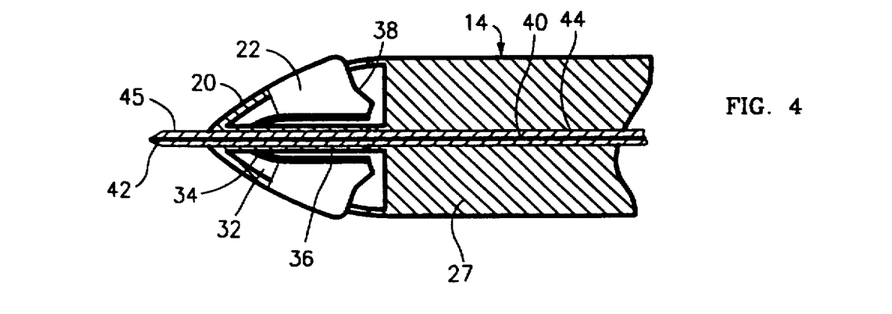
FIG. 4 is a cross-sectional view of the distal portion of the cutting catheter with the blades illustrated in a retracted position.
Figure 5:
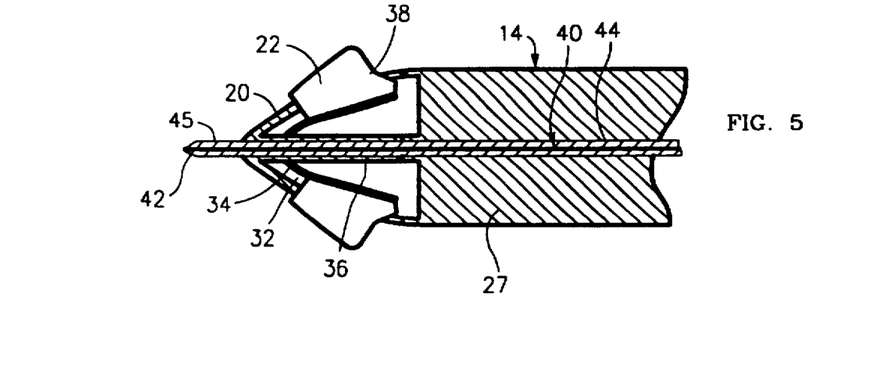
FIG. 5 is a cross-sectional view of the cutting catheter with the blades illustrated in an extended position.

The structural details of the cutting catheter 14 may be better appreciated with reference to FIGS. 4 and 5. More specifically, the cutting catheter 14 includes a cutting catheter body 27 having a hollow chamber 32. A spring carrier 34 is positioned inside the hollow chamber 32 and forms the mounting point for each of the blades 22. The spring carrier 34 is attached to a projection 36 which is attached to the cutting catheter 14.

Functionally, the combination of the chamber 32, spring carrier 34, and projection 36 allows each of the blades 22 to move between a first position (illustrated in FIG. 4) where the blades 22 are substantially contained within the chamber 32 and a second position (illustrated in FIG. 5) where the blades 22 project radially from the surface of the cutting catheter 14. Additionally, the spring carrier 34 is formed from a resilient material which biases the blades 22 to preferentially adopt the second or extended position. In this fashion, the blades 22 may be compressively retracted into the chamber 32, as shown in FIG. 4, to allow the cutting catheter 14 to advance through the deployment lumen 28. When the distal end 20 of the cutting catheter 14 is advanced to project from the deployment aperture 30, however, the blades 22 expand to adopt the second, or extended position of FIG. 5.

Importantly, each blade 22 is formed to include a sloping rear shoulder 38. The sloping rear shoulder 38 is shaped and dimensioned to engage the deployment aperture 30 when the cutting catheter 14 is withdrawn into the deployment lumen 28. The engagement between the sloping rear shoulder 38 and the deployment aperture 30 applies a force to each blade 22 causing the blades 22 to adopt the first position, shown in FIG. 4, where the blades 22 are substantially contained within the chamber 32.

Figure 6:
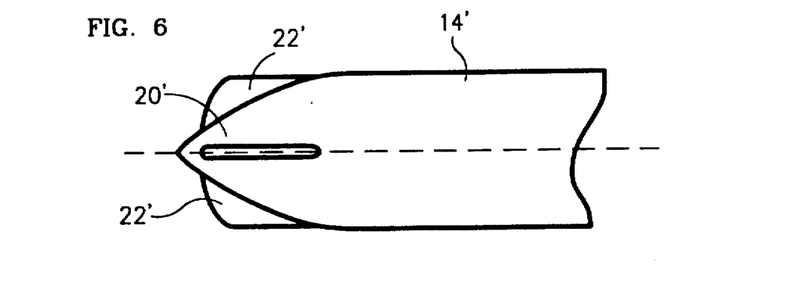
FIG. 6 is a side plan view of the distal portion of another embodiment of a cutting catheter having features of the present invention.

The cutting catheter 14 of FIGS. 4 and 5 provides a combined incisor/dilator which is adapted to advance through the deployment lumen 28. It may be appreciated, however, that other embodiments are possible for the cutting catheter 14. For example, in FIG. 6 an alternate embodiment for the cutting catheter 14 is shown and designated 14'. In this embodiment, the cutting catheter 14' is formed with a distal end 20' which is pointed and a plurality of spaced apart blades 22'. The blades 22', however, are fixed to distal end 20' and are not retractable, as was the case with blades 22 of cutting catheter 14. Instead, blades 22' are shaped and dimensioned to project from distal end 20' but not to exceed the width of cutting catheter 14'. In this way cutting catheter 14' may be advanced through deployment lumen 28 without danger of contact between blades 22' and deployment lumen 28.

Referring again to FIGS. 2–5, it may be seen that the present invention also includes a cutting guidewire 40. The cutting guidewire 40 has a sharpened cutting guidewire tip 42 and is formed from a resilient and flexible material, such as stainless steel. As shown in FIGS. 4 and 5, the cutting catheter 14 is formed to include a cutting catheter lumen 44 through which the cutting guidewire 40 may be inserted. This allows the cutting guidewire tip 42 of the cutting guidewire 40 to be selectively extended from the distal end 20 of the cutting catheter 14.

Additionally, as can best be seen with reference to FIGS. 4 and 5, the cutting guidewire 40 can include a cutting guidewire lumen 45. The cutting guidewire lumen 45 can be in fluid communication with a source of medication 66, a source of contrast medium 68, and/or a pressure sensor 70. This allows for medications or a contrast medium to be selectively released from the cutting guidewire tip 42. Further, it allows for pressure measurements to be taken at the cutting guidewire tip 42. With the pressure measurements, the location of the cutting guidewire tip 42 can be properly evaluated. This ensures that the cutting guidewire tip 42 is properly positioned prior to deploying the cutting catheter 14.

Alternate embodiments of the device 10 are possible. For example, referring to FIGS. 7 and 8, it may be seen that the anchor means 24 includes a cylindrical sleeve 46 which is attached to the distal end 16 of positioning catheter 12. Cylindrical sleeve 46 is preferably formed from a wire mesh and has a distal sleeve end 48 and a proximal sleeve end 50. The proximal sleeve end 50 is attached to the distal end 16 of positioning catheter 12. A grommet 52, is attached to the distal sleeve end 48. Preferably, the grommet 52 is formed to allow for the passage of fluid through the cylindrical sleeve 46. For example, in the case of the grommet 52 shown in FIGS. 7 and 8, there are a series of holes or ports 54, through which fluid may pass.

Figure 7:
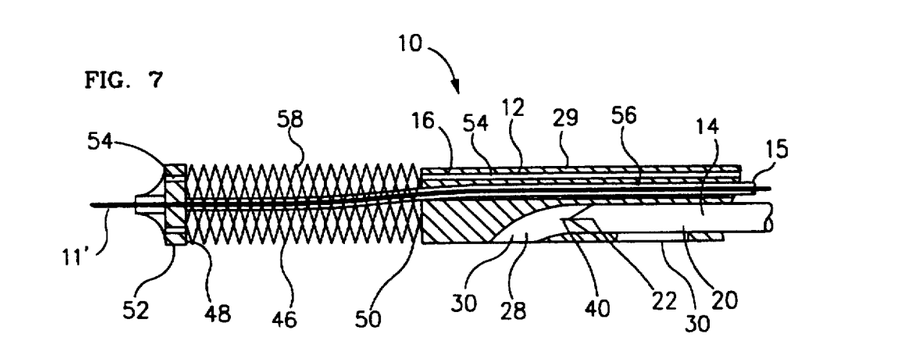
FIG. 7 is a cross-sectional view of the distal portion of another embodiment of a device having features of the present invention.
Figure 8:
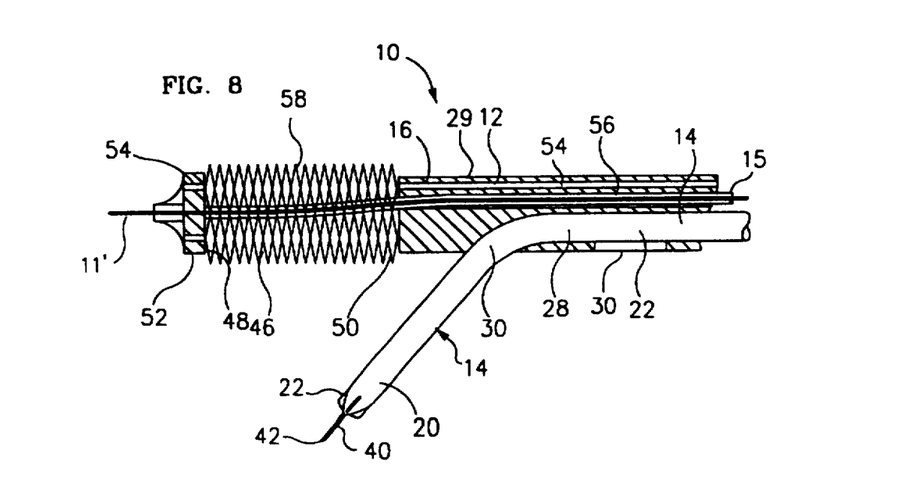
FIG. 8 is a cross-sectional view of the embodiment illustrated in FIG. 7, with a cylindrical sleeve shown in an expanded configuration and the cutting catheter advanced to project from the positioning catheter.

Continuing with FIGS. 7 and 8, it may be seen that the alternate embodiment for the positioning catheter 12 is formed to include an actuator lumen 56 in place of the inflation lumen 26 of positioning catheter 12. Additionally, it may be seen that an actuator wire 58 passes through the actuator lumen 56 and connects to the grommet 52. In this embodiment, the positioning guidewire 11 extends through the positioning guidewire lumen 15 in the actuator wire 58.

Importantly, the actuator wire 58 is movable in translation within the actuator lumen 56. As a result, the actuator wire 58 may be utilized to move the grommet 52 translationally in line with the longitudinal axis of the positioning catheter 12. Translational movement of the grommet 52 causes translational movement of the distal sleeve end 48. In this fashion, the actuator wire 58 moves the distal sleeve end 48 translationally towards or translationally away from, the distal end 16 of the positioning catheter 12. Movement of this type may be visualized by comparison of FIG. 7 and FIG. 8. In particular, it may be seen in FIG. 8 that cylindrical sleeve 46 has a shorter overall length than cylindrical sleeve 46 shown in FIG. 7.

Comparison of FIGS. 7 and 8 also shows that the decrease in overall length of the cylindrical sleeve 46, as shown in FIG. 8, is accompanied by a corresponding increase in the overall width of the cylindrical sleeve 46. Alternatively stated, it may be appreciated that the translational movement of the distal sleeve end 48 towards the distal end 16 of the positioning catheter 12 has compressively expanded the cylindrical sleeve 46 of FIG. 8. In this fashion, the actuator wire 58 may be manipulated to selectively expand the cylindrical sleeve 46.

Figure 9:
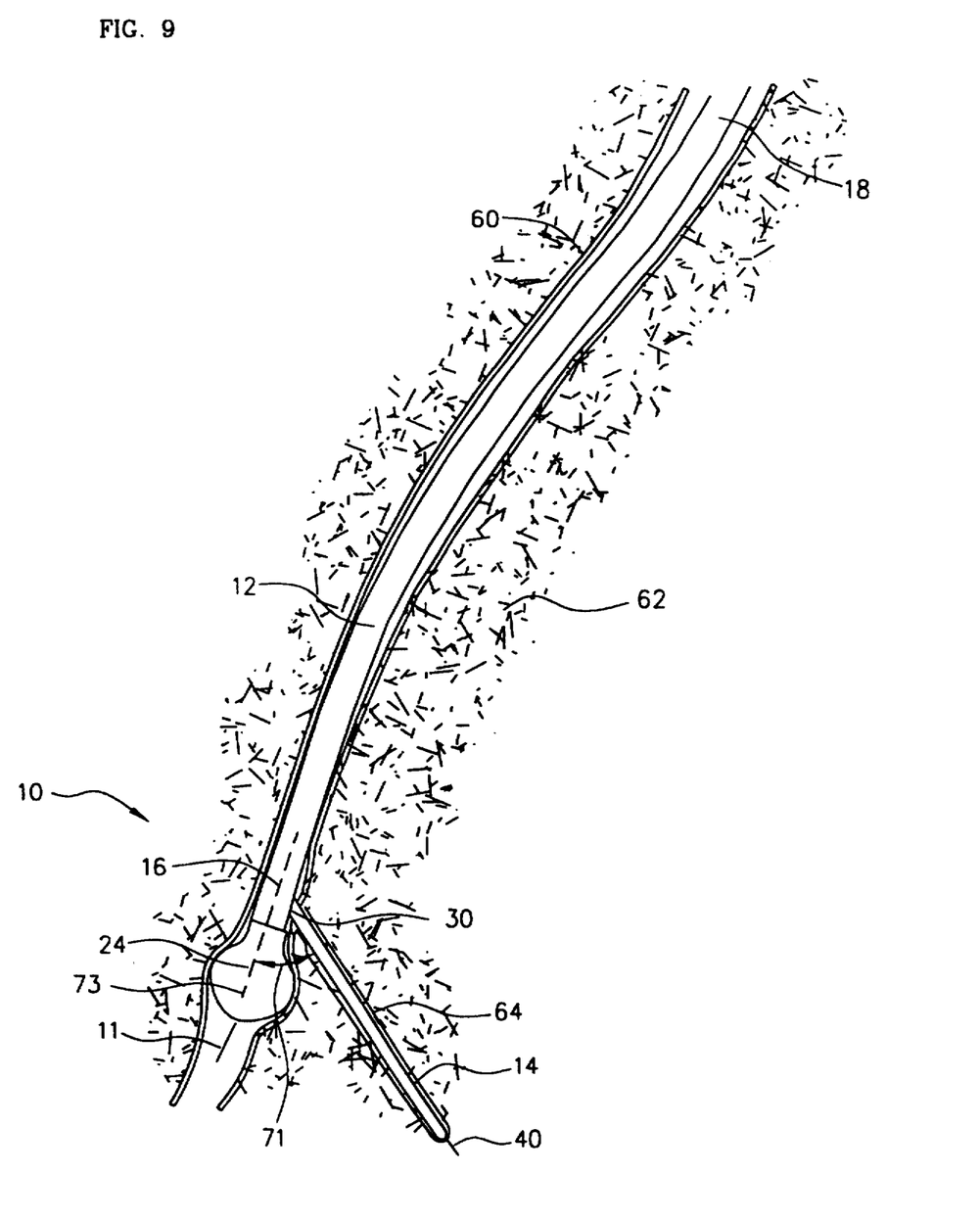
FIG. 9 is a plan view of a device having features of the present invention shown operationally positioned within a cardiac vessel.

FIG. 9 illustrates one embodiment of the device operationally positioned within a vessel 60. As illustrated in FIG. 9, the anchor means 24 is a balloon which is expanded to contact the circumference of the vessel 60 and anchor the positioning catheter 12 in the vessel 60. Subsequently, a perfusion channel 64 is created in the tissue 62 with the cutting catheter 14. As illustrated in FIG. 9, the perfusion channel 64 is at an angle 71 of between approximately twenty degrees to eighty degrees (20°–80°) relative to a centerline 73 of the positioning catheter 12 proximate to where the cutting catheter 14 extends away from the positioning catheter 12.

Figure 10:
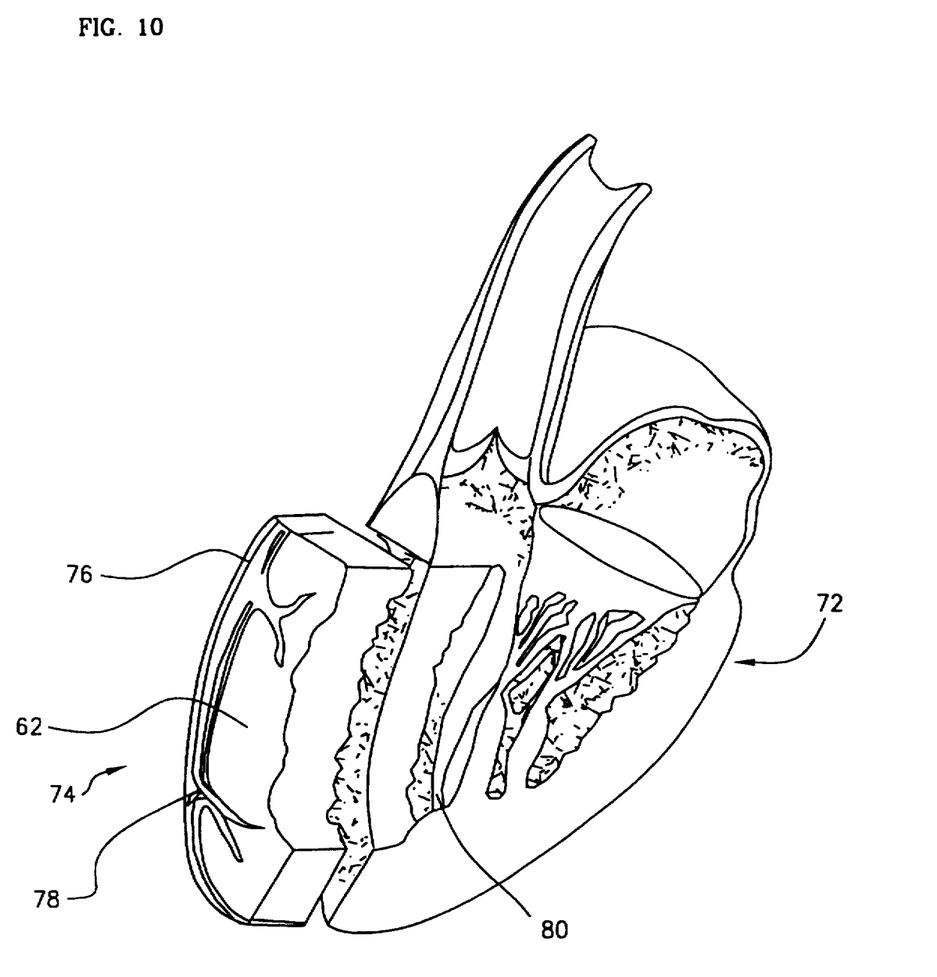
FIG. 10 is a perspective illustration of a human heart with an operational section of the heart illustrated away from the rest of the heart.

FIG. 10 is an illustration of a human heart 72. An operational section 74 of the heart 72 is illustrated away from the rest of the heart 72. As illustrated in FIG. 10, the heart includes a coronary artery 76, a ventricular cavity 80, and in this case a stenotic area 78.

Figure 11:
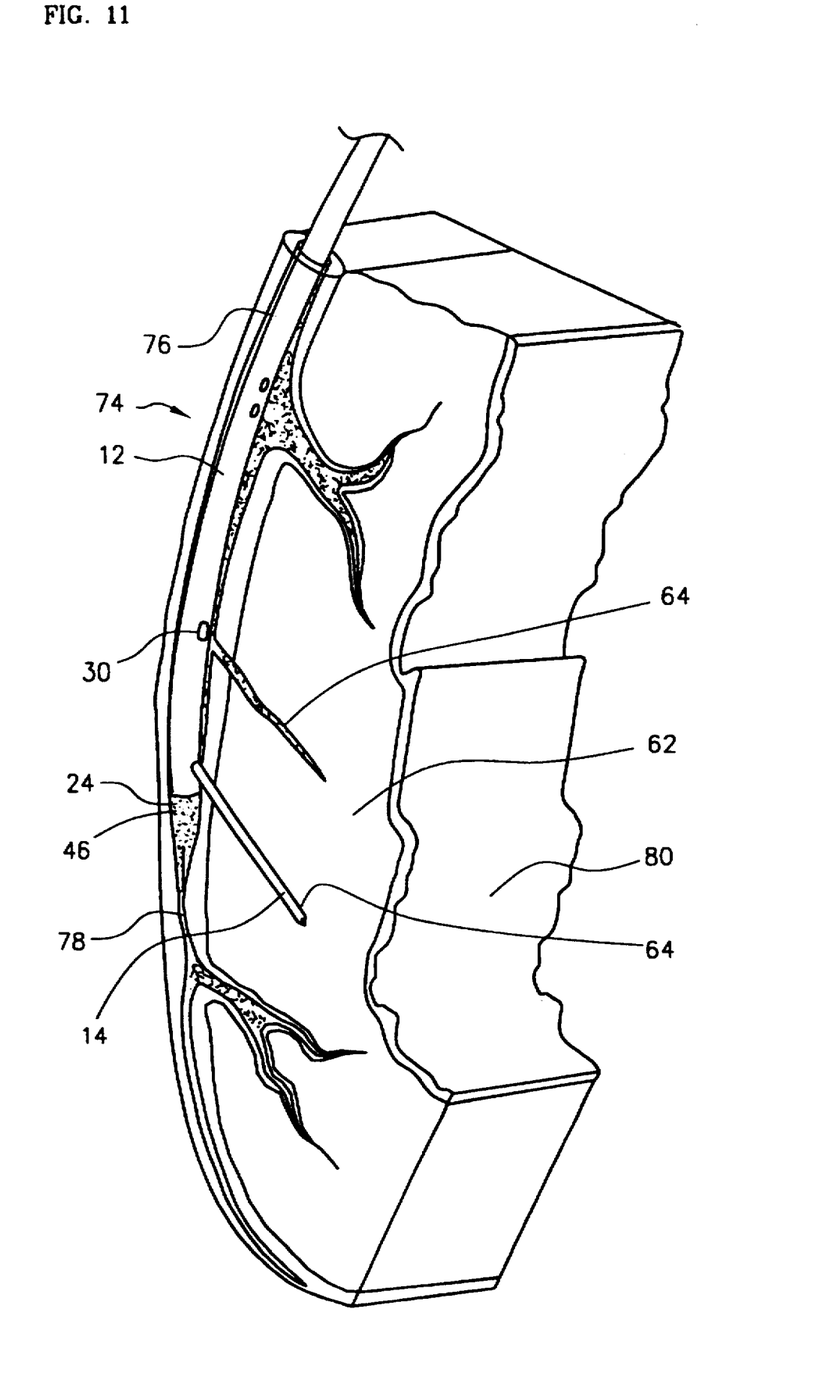
FIG. 11 is an enlarged, perspective of a device having features of the present invention positioned with the operational section of the heart from FIG. 10.

FIG. 11 illustrates an enlarged view of the operational section 74 of the heart from in FIG. 10. Also, a device 10 having features of the present invention is shown operationally positioned in the coronary artery 76. FIG. 11 illustrates that the anchor means 24 include the cylindrical sleeve 46 which is expanded to anchor the positioning catheter 12. Subsequently, a pair of perfusion channels 64 have been bored and created in the myocardial tissue 62 using the cutting catheter 14. As illustrated in FIG. 11, the perfusion channels 64 do not extend all the way through the myocardial tissue 62 into the cavity 80 of the heart 72. Instead, each perfusion channel 64 extends a distance of between approximately one centimeter to five centimeters (1.0 cm–5.0 cm), depending upon the angle of the perfusion channel 64. Further, each perfusion channel 64 has a width of between approximately two millimeters to three millimeters (2.0 mm–3.0 mm).

Figure 12:
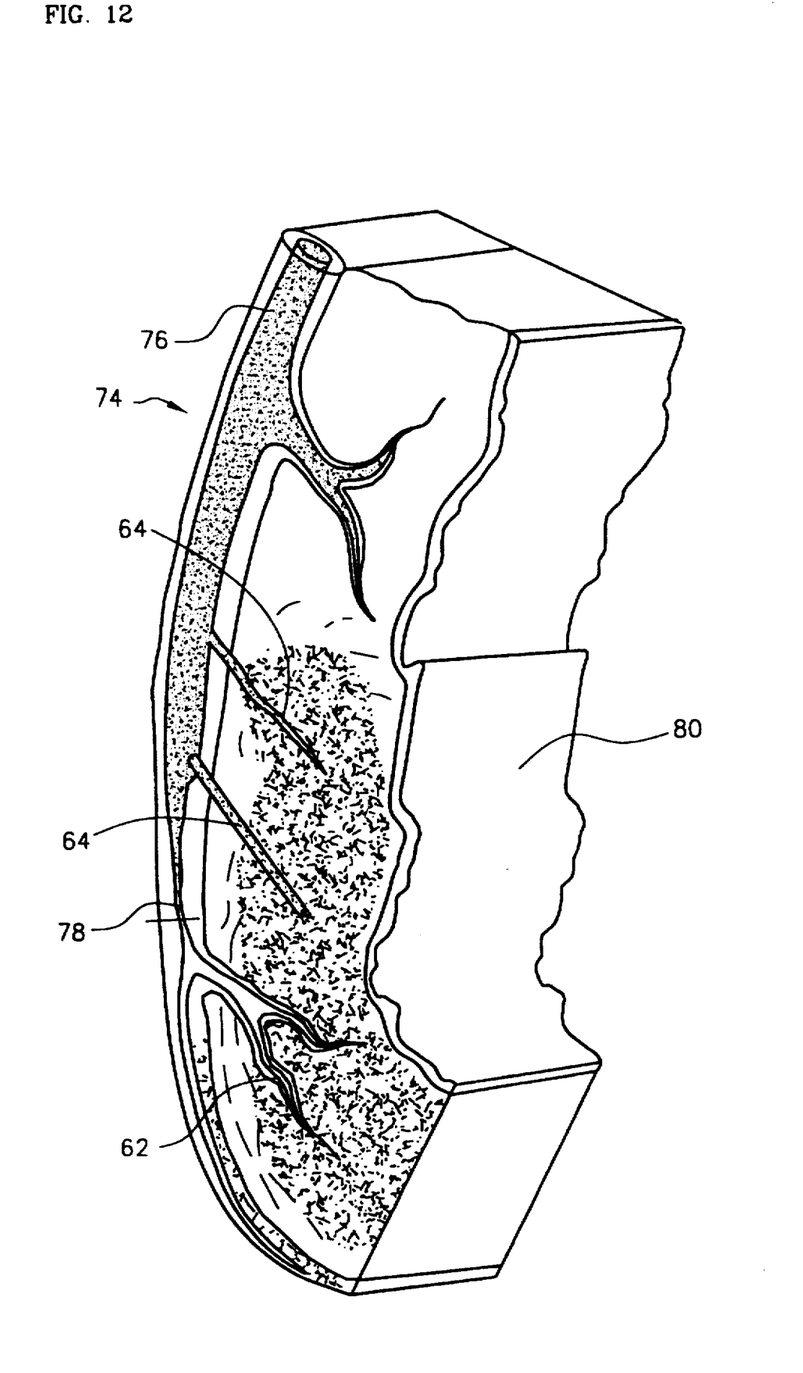
FIG. 12 is an enlarged, perspective view of the operational section of the heart from FIG. 10 after a procedure performed in accordance with the present invention.

FIG. 12 illustrates the operational section 74 after the procedure has been performed and the device 10 has been removed. From FIG. 12, it is illustrated that perfusion channels 64 are supplying blood to the myocardial tissue 62. This allows the device 10 of the present invention to treat an occlusion 78 of the coronary artery 76 which restricts the blood flow to the myocardial tissue 62 of the heart 72. Thus, the coronary artery 76 is better able to supply blood to the myocardial tissue 62 and the heart 72 is able to function more efficiently.

Operation

Operation of the present invention, is probably best appreciated with initial reference to FIGS. 9 and 11. First, the positioning guidewire 11 is inserted into a vessel 60. Generally, the particular arterial vessel 60 chosen will be one that terminates within the myocardial tissue 62 and will generally be connected to a number of smaller vessels (not shown) some of which may be partially or fully occluded. Next, the positioning catheter 12 is inserted into the arterial vessel 60 over the positioning guidewire 11. The insertion or advancement of the positioning catheter 12 will continue until the distal end 16 and deployment apertures 30 of the positioning catheter 12 are adjacent to a target area where one or more perfusion channels 64 are to be established.

Once the positioning catheter 12 is properly positioned, the anchor means 24 is expanded to anchor the distal end 16 of the positioning catheter 12 in the vessel 60. Next, the cutting guidewire 40 may be advanced through the deployment lumen 28. Depending upon the desired location of the perfusion channel 64, the cutting guidewire tip 42 is controlled to exit from the desired deployment aperture 30. Subsequently, the cutting catheter 14 is advanced through the deployment lumen 28 over the cutting guidewire 40. This causes the distal end 20 of the cutting catheter 14 to be projected from the deployment aperture 30 of the positioning catheter 12. As the cutting catheter 14 is projected from the deployment aperture 30, the distal end 20 of the cutting catheter 14 cuts a perfusion channel 64 in the myocardial tissue 62. The cutting of the perfusion channel 64 is aided by the blades 22 which incise the myocardial tissue 62 and the cutting catheter body 27 which dilates the myocardial tissue 62. Once the perfusion channel 64 has been established, the cutting catheter 14 may be withdrawn from the tissue 62 and rerouted through another deployment aperture 30 to create another perfusion channel 64.

Advancement of the cutting catheter 14 through the myocardial tissue 62 may be facilitated by use of the cutting guidewire 40. In more detail, it may be appreciated that by selectively extending the cutting guidewire 40 from the cutting catheter 14, a pilot hole may be established through the myocardial tissue 62. The cutting catheter 14 may then be advanced over the cutting guidewire 40 to enlarge the pilot hole into the perfusion channel 64. The process of advancing the cutting guidewire 40 followed by advancing the cutting catheter 14 over the cutting guidewire 40 may be repeated until the perfusion channel 64 has reached the desired depth. As provided above, typically each perfusion channel 64 has a diameter between approximately two millimeters to three millimeters (2.0 mm–3.0 mm) and a depth of between approximately one centimeter to five centimeters (1.0 cm–5.0 cm), depending upon the angle of the perfusion channel 64. Further, as illustrated in FIG. 11, each perfusion channel 64 does not extend through the myocardial tissue 62 into the ventricular cavity 80. FIG. 12 illustrates that blood flow to the myocardial tissue 62 from the coronary artery 76 is enhanced by this procedure.

Importantly, medication such as zylocaine, cardiac medications, and angiogenesis agents, can be released from the cutting guidewire tip 42 into the cardiac muscle 62 prior to, during, or after the procedure. Alternately, a contrast medium can be released from the cutting guidewire tip 42 to determine the location of the cutting guidewire tip 42. Further, pressure at the cutting guidewire tip 42 can be measured to determine whether the cutting guidewire tip 42 is in the proper location prior to inserting the cutting guidewire 40.

In some cases it may be desirable to deploy a stent (not shown), or other prosthesis, to support the newly formed perfusion channel 64. In such cases, the stent may be advanced through the deployment lumen 28 and emitted through the deployment aperture 30 to be positioned by any method well known in the pertinent art.

While the particular device 10 as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for treating a deficiency of blood flow from a coronary artery to a cardiac muscle, the method comprising the steps of:

advancing a positioning catheter into the coronary artery;

anchoring a portion of the positioning catheter in the coronary artery;

advancing a cutting guidewire into the cardiac muscle; and creating a perfusion channel with a cutting catheter which extends away from the positioning catheter, the perfusion channel extending from the artery into only a portion of the cardiac muscle, the perfusion channel allowing blood flow from the coronary artery to the cardiac muscle.

2. The method of claim 1 wherein the step of creating a perfusion channel includes creating a perfusion channel having a diameter of between approximately two millimeters and three millimeters.

3. The method of claim 1 wherein the step of creating a perfusion channel includes creating a perfusion channel at an angle of between approximately twenty degrees and eighty degrees relative to a center-line of the positioning catheter proximate where the cutting catheter extends away from the positioning catheter.

4. The method of claim 1 including the step of releasing a medication from the cutting guidewire into the cardiac muscle.

5. The method of claim 1 including the step of releasing a contrast medium from the cutting guidewire into the cardiac muscle to determine the location of the guidewire.

6. The method of claim 4 including the step of determining the location of a cutting guidewire tip of the cutting guidewire by measuring the pressure at a cutting guidewire tip to determine the location of a cutting guidewire tip of the cutting guidewire.

7. The method of claim 1 wherein the step of creating a perfusion channel includes utilizing a cutting catheter having a plurality of spaced apart blades which extend substantially radially from a cutting catheter body of the cutting catheter.

8. The method of claim 1 including the step of creating a second perfusion channel extending from the coronary artery into only a portion of the cardiac muscle.

9. The method of claim 8 wherein the step of creating a second perfusion channel includes creating a second perfusion channel having a diameter of between approximately two millimeters and three millimeters.

* * * * *